United States Patent [19]

Wade et al.

[11] 4,012,374

[45] Mar. 15, 1977

[54] 1-[[4-PHENYL-PIPERIDINYL (OR TETRAHYDROPYRIDINYL)]ALKYL]-2,6-PIPERIDINEDIONE AND ANALOGS

[75] Inventors: Peter C. Wade, Pennington, N.J.; B. Richard Vogt, Yardley, Pa.

[73] Assignee: E. R. Squibb & Sons, Inc., Princeton, N.J.

[22] Filed: Sept. 29, 1975

[21] Appl. No.: 617,473

[52] U.S. Cl. .............. 260/239.3 R; 260/281 GN; 260/293.71; 260/295 D; 260/294.9; 424/263; 424/267; 260/294.8 G

[51] Int. Cl.² .................................. C07D 401/06

[58] Field of Search ............ 260/239.3 R, 281 GN, 260/293.69, 293.71, 295 D, 294.8 R, 294.9, 294.8 G

[56] References Cited

UNITED STATES PATENTS

| | | | |
|---|---|---|---|
| 2,833,777 | 5/1958 | Rorig | 260/293.71 |
| 3,171,839 | 3/1965 | Rorig | 260/281 GN |
| 3,226,392 | 12/1965 | Carabateas | 260/293.69 |
| 3,481,935 | 12/1969 | Tomcufcik et al. | 260/293.69 |
| 3,714,159 | 1/1973 | Janssen et al. | 260/293.71 |
| 3,884,916 | 5/1975 | Janssen et al. | 260/293.71 |

*Primary Examiner*—Henry R. Jiles
*Assistant Examiner*—Robert T. Bond
*Attorney, Agent, or Firm*—Lawrence S. Levinson; Merle J. Smith; Donald J. Barrack

[57] ABSTRACT

Compounds having the formula

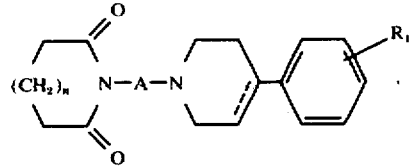

wherein A is a straight or branched chain alkylene group; $R_1$ is hydrogen, halogen, alkyl, alkoxy, alkylthio, trifluoromethyl, nitro, amino, or cyano; and $n$ is 0, 1, or 2; are useful central nervous system depressants.

6 Claims, No Drawings

1-[[4-PHENYL-PIPERIDINYL (OR TETRAHYDROPYRIDINYL)]ALKYL]-2,6-PIPERIDINEDIONE AND ANALOGS

SUMMARY OF THE INVENTION

Useful central nervous system depressant activity is exhibited by compounds having formula

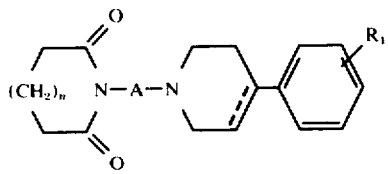  I

In formula I, and throughout the specification, the symbols are as defined below.

$R_1$ can be hydrogen, halogen, alkyl, alkoxy, alkylthio, trifluoromethyl, nitro, amino, or cyano;

A can be a straight or branched chain alkylene group having 1 to 8 carbon atoms; and n can be 0, 1, or 2.

The broken line in the piperidine nucleus represents the optional presence of ethylenic unsaturation.

The term "alkyl", as used throughout the specification, refers to alkyl groups having 1 to 4 carbon atoms.

The term "alkoxy", as used throughout the specification, refers to groups having the formula Y-O- wherein Y is alkyl as defined above.

The term "alkylthio", as used throughout the specification, refers to groups having the formula Y-S- wherein Y is alkyl as defined above.

The term "halogen", as used throughout the specification, refers to fluorine, chlorine, bromine, and iodine; fluroine, chlorine, and bromine are the preferred halogens.

DETAILED DESCRIPTION OF THE INVENTION

The compounds of formula I, and their pharmaceutically acceptable acid addition salts, are useful in mammalian species such as rats, dogs, monkeys, and others, as central nervous system depressants, and can be used as tranquilizers for the relief of anxiety and tension states in the same manner as chlordiazepoxide. For this purpose, the compounds of this invention can be administered parenterally in single or divided doses of about 0.1 to 100 milligrams per kilogram of body weight per day, preferably about 0.5 to 15 milligrams per kilogram of body weight, two to four daily.

The components of formula I, and their pharmaceutically acceptable acid addition salts, are also useful for the treatment of inflammation in mammalian species, e.g., rats, dogs, cats, monkeys, etc. Joint tenderness and stiffness (in conditions such as rheumatoid arthritis) can be relieved by the above-described compounds. The compounds of this invention are formulated for use as anti-inflammatory agents according to accepted pharmaceutical practice in oral dosage forms such as tablets, capsules, elixirs or powders, or in an injectable form in a sterile aqueous vehicle prepared according to conventional pharmaceutical practice. The compounds of this invention can be administered in amounts of 100 milligrams per kilogram of animal body weight per day to 2 grams per kilogram of animal body weight per day, preferably 100 milligrams per kilogram of animal body weight per day to 1 gram per kilogram of animal body weight per day.

The products of formula I, wherein A is an alkylene group having 2 to 8 carbon atoms, can be prepared using as starting materials compounds having the formulas

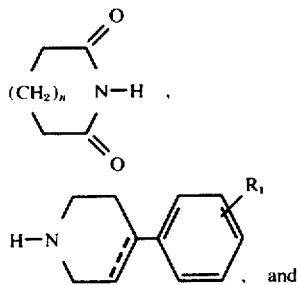

and $$X' - A' - X. \quad \text{IV}$$

In formula IV, and throughout the specification, the symbol A' can be a straight or branched chain alkylene group having 2 to 8 carbon atoms and the symbols X and X' can be the same or different and can be halogen (preferably chlorine or bromine), alkylsulfonate (e.g., methanesulfonate or arylsulfonate (e.g., toluenesulfonate).

Reaction of a compound of formula II with a compound of formula IV yields an intermediate having the formula

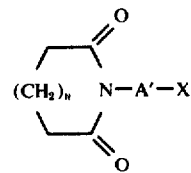  V

The reaction can be run in a polar organic solvent, e.g., dimethylsulfoxide or dimethhylformamide, in the presence of alkali.

Reaction of an intermediate of formula V with a pyridine derivative of formula III yields the compounds of formula I wherein A is an alkylene group having 2 to 8 carbon atoms. The reaction can be run in an organic solvent, e.g., benzene, toluene, etc., preferably in the presence of an organic or inorganic base, e.g., a tertiary amine such as ethyldiisopropylamine or an alkali metal carbonate such as sodium carbonate. While reaction conditions are not critical, the reaction will most conveniently be run at the reflux temperature of the solvent.

Alternatively, the products of formula I, wherein A is an alkylene group having 2 to 8 carbon atoms, can be prepared by first reacting a compound of formula II with an appropriate base, e.g., potassium hydroxide or thallous ethoxide. The resultant salt is reacted with a compound having the formula

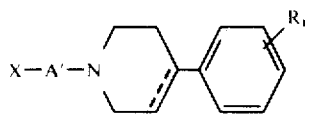

to yield the products of formula I wherein A is other than methylene.

In still another method for preparing the compounds of formula I wherein A is other than methylene, a compound having the formula

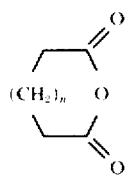

is first reacted with a compound having the formula VIII

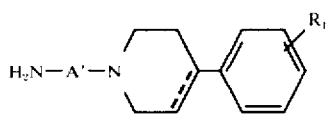

to yield a compound having the formula

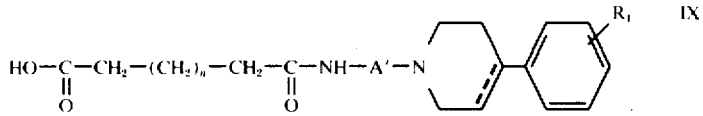

Ring closure of a compound of formula IX using a dehydrating agent such as thionyl chloride, acetic anhydride or phosphorous oxychloride and/or heat yields the products of formula I wherein A is other than methylene.

The products of formula I wherein a is methylene are prepared using the Mannich reaction. A compound of formula II is reacted with a piperidine derivative of formula III, or its hydrohalogen salt, in the presence of formaldehyde or paraformaldehyde to yield the desired product. The reaction is run in a polar organic solvent such as dimethylformamide.

Additional procedures for preparing the compounds of this invention will readily apparent to a person skilled in the art. For example, compounds of formula I wherein $R_1$ is amino, cyano, or halogen can be prepared from the corresponding nitro compounds using well known reactions. The nitro group can be reduced to an amino group using stannous chloride and a mineral acid such as hydrochloric acid, and the amino group can be converted to a halogen or cyano group using the Sandmeyer reaction.

The compounds of formula I can be converted into their pharmaceutically acceptable acid addition salts using procedures well known in the art. Exemplary of the salts contemplated are the hydrohalides, especially the hydrochloride and hydrobromide which are preferred. Other inorganic salts contemplated are the nitrate, phosphate, sulfate and the like. Organic salts are also contemplated; illustrative are the tartrate, maleate, fumarate, citrate, succinate, methanesulfonate, benzenesulfonate, toluenesulfonate, and the like.

The following examples are specific embodiments of this invention.

EXAMPLE 1

1-[4-[3,6-Dihydro-4-phenyl-1(2H)pyridinyl]butyl]-2,6-piperidinedione, hydrochloride (1:1)

A. N-(4-Bromobutyl)glutarimide

Sodium (5g) is dissolved in 100 ml of absolute ethanol and the resulting sodium ethoxide solution is added to a solution of 23g of glutarimide in 160 ml of warm absolute ethanol. A precipitate forms almost immediately, and after allowing the mixture to cool to 25° C while stirring, the solvent is removed under vacuum. To the residue is added 70 ml of dimethylformamide and 60 ml of 1,4-dibromobutane and the mixture is refluxed for 10 minutes. The solvent is removed under vacuum and the residue is shaken with hexane to remove excess 1,4-dibromobutane. The hexane layer is decanted, the residue taken up in ether, and the insoluble material filtered off. The ethereal filtrate is washed with 10% sodium hydroxide, 10% hydrochloric acid, and water, and dried over sodium sulfate. The solvent is removed under vacuum to yield 26g of N-(4-bromobutyl)glutarimide as an oil.

B. 1-[4-[3,6-Dihydro-4-phenyl-1(2H)pyridinyl]butyl]-2,6-piperidinedione, hydrochloride (1:1)

4-Phenyl-1,2,3,6-tetrahydropyridine, hydrochloride (10g) is converted to its free base and mixed with 11 0g of N-(4-bromobutyl)glutarimide and 18g of sodium carbonate in 200 ml of toluene. The mixture is refluxed for 5 hours, cooled to 25° C, and 50 ml of water is added. After stirring for 15 minutes, the layers are separated and the organic layer is filtered through fritted glass and extracted with 10% hydrochloric acid. The acid layer is made alkaline (pH 10) with sodium hydroxide producing an insoluble gum that crystallizes on standing. The supernatant is decanted and the residue is recrystallized by dissolving in methanol and slowly diluting with an equal volume of water. An oil is produced that crystallizes on standing.

The crystals are filtered off and taken up in hot ether/ethanol (10:1). The solution is treated with a 10% excess of ethereal hydrogen chloride precipitating the salt as a gum. After 30 minutes the ether is decanted and the gum taken up in a small amount of ethanol. Slow addition of a large amount of ether gives the salt as a fine granular precipitate.

The salt is filtered off and dried at 50° C (0.1 mm of Hg) for 4 hours to yield 10.4g of the title compound, melting point 159.5° C–161° C.

EXAMPLES 2–55

Following the procedure of Example 1, but substituting the compound listed in column I for glutarimide, the compound listed in column II for 1,4-dibromobutane, and the compound listed in column III for 4-phenyl-1,2,3,6-tetrahydropyridine, hydrochloride, the compound listed in column IV is obtained.

| Example | Column I | Column II | Column III | Column IV |
|---|---|---|---|---|
| 2 | glutarimide | 1,2-dibromoethane | 4-(4-chlorophenyl)-1,2,3,6-tetrahydropyridine | 1-[2-[3,6-dihydro-4-(4-chlorophenyl)-1(2H)pyridinyl]ethyl]-2,6-piperidinedione, hydrochloride |
| 3 | glutarimide | 1,3-dibromopropane | 4-(4-bromophenyl)-1,2,3,6-tetrahydropyridine | 1-[3-[3,6-dihydro-4-(4-bromophenyl)-1(2H)pyridinyl]propyl]-2,6-piperidinedione, hydrochloride |
| 4 | glutarimide | 1,5-dibromopentane | 4-(2-methylphenyl)-1,2,3,6-tetrahydropyridine | 1-[5-[3,6-dihydro-4-(2-methylphenyl)-1(2H)pyridinyl]pentyl]-2,6-piperidinedione, hydrochloride |
| 5 | glutarimide | 1,6-dibromohexane | 4-(3-methoxyphenyl)-1,2,3,6-tetrahydropyridine | 1-[6-[3,6-dihydro-4-(3-methoxyphenyl)-1(2H)pyridinyl]hexyl]-2,6-piperidinedione, hydrochloride |
| 6 | glutarimide | 1,7-dibromoheptane | 4-(4-methylthiophenyl)-1,2,3,6-tetrahydropyridine | 1-[7-[3,6-dihydro-4-(4-methylthiophenyl)-1(2H)pyridinyl]heptyl]-2,6-piperidinedione, hydrochloride |
| 7 | glutarimide | 1,8-dibromooctane | 4-(4-trifluoromethylphenyl)-1,2,3,6-tetrahydropyridine | 1-[8-[3,6-dihydro-4-(4-trifluoromethylphenyl)-1(2H)pyridinyl]octyl]-2,6-piperidinedione, hydrochloride |
| 8 | glutarimide | 1,3-dibromo-2-methylpropane | 4-(3-nitrophenyl)-1,2,3,6-tetrahydropyridine | 1-[3-[3,6-dihydro-4-(3-nitrophenyl)-1(2H)pyridinyl]-2-methylpropyl]-2,6-piperidinedione, hydrochloride |
| 9 | glutarimide | 1,2-dibromoethane | 4-(2-aminophenyl)-1,2,3,6-tetrahydropyridine | 1-[2-(3,6-dihydro-4-(2-aminophenyl)-1(2H)pyridinyl]ethyl]-2,6-piperidinedione, hydrochloride |
| 10 | glutarimide | 1,3-dibromopropane | 4-(2-cyanophenyl)-1,2,3,6-tetrahydropyridine | 1-[3-[3,6-dihydro-4-(2-cyanophenyl)-1(2H)pyridinyl]propyl]-2,6-piperidinedione, hydrochloride |
| 11 | succinimide | 1,2-dibromoethane | 4-phenyl-1,2,3,6-tetrahydropyridine | 1-[2-[3,6-dihydro-4-phenyl-1(2H)pyridinyl]ethyl]-2,5-pyrrolidinedione, hydrochloride |
| 12 | succinimide | 1,8-dibromooctane | 4-(2-chlorophenyl)-1,2,3,6-tetrahydropyridine | 1-[8-[3,6-dihydro-4-(2-chlorophenyl)-1(2H)pyridinyl]octyl]-2,5-pyrrolidinedione, hydrochloride |
| 13 | succinimide | 1,3-dibromopropane | 4-(2-ethylphenyl)-1,2,3,6-tetrahydropyridine | 1-[3-[3,6-dihydro-4-(2-ethylphenyl)-1(2H)pyridinyl]propyl]-2,5-pyrrolidinedione, hydrochloride |
| 14 | succinimide | 1,4-dibromobutane | 4-(2-ethoxyphenyl)-1,2,3,6-tetrahydropyridine | 1-[4-[3,6-dihydro-4-(2-ethoxyphenyl)-1(2H)pyridinyl]butyl]-2,5-pyrrolidinedione, hydrochloride |
| 15 | succinimide | 1,5-dibromopentane | 4-(2-ethylthiophenyl)-1,2,3,6-tetrahydropyridine | 1-[5-[3,6-dihydro-4-(2-ethylthiophenyl)-1(2H)pyridinyl]pentyl]-2,5-pyrrolidinedione, hydrochloride |
| 16 | succinimide | 1,6-dibromohexane | 4-(2-trifluoromethylphenyl)- | 1-[6-[3,6-dihydro-4-(2-trifluoromethylphenyl)-1(2H)pyridinyl]hexyl]-2,5-pyrrolidinedione, hydrochloride |
| 17 | succinimide | 1,7-dibromoheptane | 4-(4-nitrophenyl)-1,2,3,6-tetrahydropyridine | 1-[7-[3,6-dihydro-4-(4-nitrophenyl)-1(2H)pyridinyl]heptyl]-2,5-pyrrolidinedione, hydrochloride |
| 18 | succinimide | 1,2-dibromoethane | 4-(4-aminophenyl)-1,2,3,6-tetrahydropyridine | 1-[2-[3,6-dihydro-4-(4-aminophenyl)-1(2H)pyridinyl]ethyl]-2,5-pyrrolidinedione, hydrochloride |
| 19 | succinimide | 1,5-dibromo-3-methylpentane | 4-(4-cyanophenyl)-1,2,3,6-tetrahydropyridine | 1-[5-[3,6-dihydro-4-(4-cyanophenyl)-1(2H)pyridinyl]-3-methylpentyl]-2,5-pyrrolidinedione, hydrochloride |
| 20 | adipimide | 1,2-dibromoethane | 4-phenyl-1,2,3,6-tetrahydropyridine | 1-[2-[3,6-dihydro-4-phenyl-1-(2H)pyridinyl]ethyl]-2,7-homopiperidinedione, hydrochloride |
| 21 | adipimide | 1,3-dibromopropane | 4-(4-fluorophenyl)-1,2,3,6-tetrahydropyridine | 1-[3-[3,6-dihydro-4-(4-fluorophenyl)-1(2H)pyridinyl]propyl]-2,7-homopiperidinedione, hydrochloride |
| 22 | adipimide | 1,3-dibromopropane | 4-(3-t-butylphenyl)-1,2,3,6-tetrahydropyridine | 1-[3-[3,6-dihydro-4-(3-t-butylphenyl)-1(2H)pyridinyl]propyl]-2,7-homopiperidinedione, hydrochloride |
| 23 | adipimide | 1,4-dibromobutane | 4-(3-ethoxyphenyl)-1,2,3,6-tetrahydropyridine | 1-[4-[3,6-dihydro-4-(3-ethoxyphenyl)-1(2H)pyridinyl]butyl]-2,7-homopiperidinedione, hydrochloride |
| 24 | adipimide | 1,5-dibromopentane | 4-(4-ethylthiophenyl)-1,2,3,6-tetrahydropyridine | 1-[5-[3,6-dihydro-4-(4-ethylthiophenyl)-1(2H)pyridinyl]pentyl]-2,7-homopiperidinedione, hydrocloride |
| 25 | adipimide | 1,6-dibromohexane | 4-(4-trifluoromethylphenyl)-1,2,3,6-tetrahydropyridine | 1-[6-[3,6-dihydro-4-(4-trifluoromethylphenyl)-1(2H)pyridinyl]hexyl]-2,7-homopiperidinedione, hydrochloride |
| 26 | adipimide | 1,7-dibromoheptane | 4-(3-nitrophenyl)-1,2,3,6-tetrahydropyridine | 1-[7-[3,6-dihydro-4-(3-nitrophenyl)-1(2H)pyridinyl]heptyl]-2,7-homopiperidinedione, hydrochloride |
| 27 | adipimide | 1,8-dibromooctane | 4-(3-aminophenyl)-1,2,3,6-tetrahydropyridine | 1-[-[3,6-dihydro-4-(3-aminophenyl)-1(2H)pyridinyl]octyl]-2,7-homopiperidinedione, hydrochloride |
| 28 | adipimide | 1,2-dibromoethane | 4-(3-cyanohenyl)-1,2,3,6-tetrahydropyridine | 1-[2-[3,6-dihydro-4-(3-cyanophenyl)-1(2H)pyridinyl]ethyl]-2,7-homopiperidinedione, hydrochloride |
| 29 | glutarimide | 1,2-dibromoethane | 4-(4-chlorophenyl)piperidine | 1-[2-[4-(4-chlorophenyl)piperidinyl]ethyl]-2,6-piperidinedione, hydro- |

-continued

| Example | Column I | Column II | Column III | Column IV |
|---|---|---|---|---|
| 30 | glutarimide | 1,3-dibromopropane | 4-(4-bromophenyl)piperidine | 1-[3-[4-(4-bromophenyl)piperidinyl]propyl]-2,6-piperidinedione, hydrochloride |
| 31 | glutarimide | 1,5-dibromopentane | 4-(2-methylphenyl)piperidine | 1-[5-[4-(2-methylphenyl)piperidinyl]pentyl]-2,6-piperidinedione, hydrochloride |
| 32 | glutarimide | 1,6-dibromohexane | 4-(3-methoxyphenyl)piperidine | 1-[6-[4-(3-methoxyphenyl)piperidinyl]hexyl]-2,6-piperidinedione, hydrochloride |
| 33 | glutarimide | 1,7-dibromoheptane | 4-(4-methylthiophenyl)piperidine | 1-[7-[4-(4-methylthiophenyl)piperidinyl]heptyl]-2,6-piperidinedione, hydrochloride |
| 34 | glutarimide | 1,8-dibromooctane | 4-(4-trifluoromethylphenyl)piperidine | 1-[8-[4-(4-trifluoromethylphenyl)piperidinyl]octyl]-2,6-piperidinedione, hydrochloride |
| 35 | glutarimide | 1,3-dibromo-2-methylpropane | 4-(3-nitrophenyl)piperidine | 1-[3-[4-(3-nitrophenyl)piperidinyl]-2-methylpropyl]-2,6-piperidinedione, hydrochloride |
| 36 | glutarimide | 1,2-dibromoethane | 4-(2-aminophenyl)piperidine | 1-[2-[4-(2-aminophenyl)piperidinyl]ethyl]-2,6-piperidinedione, hydrochloride |
| 37 | glutarimide | 1,3-dibromopropane | 4-(2-cyanophenyl)piperidine | 1-[3-[4-(2-cyanophenyl)piperidinyl-propyl]-2,6-piperidinedione, hydrochloride |
| 38 | succinimide | 1,2-dibromoethane | 4-phenylpiperidine | 1-[2-(4-phenylpiperidinyl)ethyl]-2,5-pyrrolidinedione, hydrochloride |
| 39 | succinimide | 1,8-dibromooctane | 4-(2-chlorophenyl)piperidine | 1-[-[4-(2-chlorophenyl)piperidinyl]octyl]-2,5-pyrrolidinedione, hydrochloride |
| 40 | succinimide | 1,3-dibromopropane | 4-(2-ethylphenyl)piperidine | 1-[3-[4-(2-ethylphenyl)pipridinyl]propyl]-2,5-pyrrolidinedione, hydrochoride |
| 41 | succinimide | 1,4-dibromobutane | 4-(2-ethoxyphenyl)piperidine | 1-[4-[4-(2-ethoxyphenyl)piperidinyl]butyl]-2,5-pyrrolidinedione, hydrochloride |
| 42 | succinimide | 1,5-dibromopentane | 4-(2-ethylthiophenyl)piperidine | 1-[5-[4-(2-ethylthiophenyl)piperidinyl]pentyl]-2,5-pyrrolidinedione, hydrochloride |
| 43 | succinimide | 1,6-dibromohexane | 4-(2-trifluoromethylphenyl)piperidine | 1-[6-[4-(2-trifluoromethylphenyl)piperidinyl]hexyl]-2,5-pyrrolidinedione, hydrochloride |
| 44 | succinimide | 1,7-dibromoheptane | 4-(4-nitrophenyl)piperidine | 1-[7-[4-(4-nitrophenyl)piperidinyl]heptyl]-2,5-pyrrolidinedione, hydrochloride |
| 45 | succinimide | 1,2-dibromoethane | 4-(4-aminophenyl)piperidine | 1-[2-[4-(4-aminophenyl)piperidinyl]ethyl]-2,5-pyrrolidinedione, hydrochloride |
| 46 | succinimide | 1,5-dibromo-3-methylpentane | 4-(4-aminophenyl)piperidine | 1-[5-[4-(4-aminophenyl)piperidinyl]-3-methylpentyl]-2,5-pyrrolidinedione, hydrochloride |
| 47 | adipimide | 1,2-dibromoethane | 4-phenylpiperidine | 1-[2-(4-phenylpiperidinyl)ethyl]-2,7-homopiperidinedione, hydrochloride |
| 48 | adipimide | 1,3-dibromopropane | 4-(3-fluorophenyl)piperidine | 1-[3-[4-(3-fluorophenyl)piperidinyl]propyl]-2,7-homopiperidinedione, hydrochloride |
| 49 | adipimide | 1,3-dibromopropane | 4-(3-t-butylphenyl)piperidine | 1-[3-[4-(3-t-butylphenyl)piperidinyl]propyl]-2,7-homopiperidinedione, hydrochloride |
| 50 | adipimide | 1,4-dibromobutane | 4-(3-ethoxyphenyl)piperidine | 1-[4-[4-(3-ethoxyphenyl)piperidinyl]butyl]-2,7-homopiperidinedine, hydrochloride |
| 51 | adipimide | 1,5-dibromopentane | 4-(4-ethylthiophenyl)piperidine | 1-[5-[4-(4-ethylthiophenyl)piperidinyl]pentyl]-2,7-homopiperidinedione, hydrochloride |
| 52 | adipimide | 1,6-dibromohexane | 4-(4-trifluoromethylphenyl)- | 1-[6-[4-(4-trifluoromethylphenyl)piperidinyl]-2,7-homopiperidinedione, hydrochloride |
| 53 | adipimide | 1,7-dibromoheptane | 4-(3-nitrophenyl)piperidine | 1-[7-[4-(3-nitrophenyl)piperidinyl]heptyl]-2,7-homopiperidinedione, hydrochloride |
| 54 | adipimide | 1,8-dibromooctane | 4-(3-aminophenyl)piperidine | 1-[8-[4-(3-aminophenyl)piperidinyl]octyl]-2,7-homopiperidinedione, hydrochloride |
| 55 | adipimide | 1,2-dibromoethane | 4-(3-cyanophenyl)piperidine | 1-[2-[4-(3-cyanophenyl)piperidinyl]ethyl]-2,7-homopiperidinedione, hydrochloride |

What is claimed is:

1. A compound having the formula

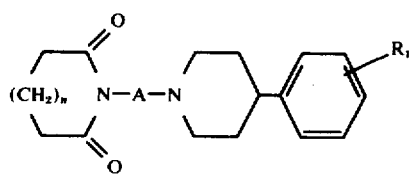

or

-continued

-continued

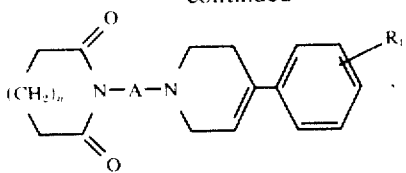

or a pharmaceutically acceptable salt thereof, wherein $n$ is 0, 1, or 2; A is an alkylene group having 1 to 8 carbon atoms; and $R_1$ is hydrogen, halogen, alkyl, alkoxy, alkylthio, trifluoromethyl, nitro, amino or cyano; wherein the alkyl, alkoxy, and alkylthio groups have 1 to 4 carbon atoms.

2. A compound in accordance with claim 1 wherein A is an alkylene group having 2 to 8 carbon atoms.

3. A compound in accordance with claim 2 wherein A is an alkylene group having 2, 3, or 4 carbon atoms.

4. A compound in accordance with claim 1 wherein A is methylene.

5. A compound in accordance with claim 1 wherein $R_1$ is hydrogen.

6. A compound in accordance with claim 1 having the formula

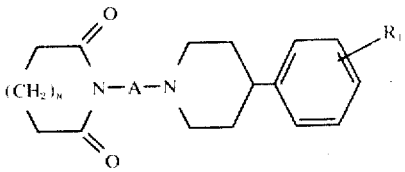

* * * * *